United States Patent
Corazza et al.

(10) Patent No.: US 10,241,120 B2
(45) Date of Patent: Mar. 26, 2019

(54) METHOD AND DEVICE FOR ASSAYING AN ANTIGEN PRESENT ON ERYTHROCYTES OR AN ANTIBODY BINDING TO AN ANTIGEN PRESENT ON ERYTHROCYTES

(71) Applicant: UNIVERSITE LIBRE DE BRUXELLES, Brussels (BE)

(72) Inventors: Francis Corazza, Schaerbeek (BE); Hanane El Kenz, Laeken (BE)

(73) Assignee: UNIVERSITE LIBRE DE BRUXELLES, Brussels (BE)

( * ) Notice: Subject to any disclaimer, the term of this patent is extended or adjusted under 35 U.S.C. 154(b) by 948 days.

(21) Appl. No.: 14/363,554

(22) PCT Filed: Dec. 5, 2012

(86) PCT No.: PCT/EP2012/074481
§ 371 (c)(1),
(2) Date: Jun. 6, 2014

(87) PCT Pub. No.: WO2013/083619
PCT Pub. Date: Jun. 13, 2013

(65) Prior Publication Data
US 2014/0363828 A1 Dec. 11, 2014

(30) Foreign Application Priority Data
Dec. 6, 2011 (EP) ...................................... 11192236

(51) Int. Cl.
*G01N 33/53* (2006.01)
*G01N 33/80* (2006.01)

(52) U.S. Cl.
CPC .................................... *G01N 33/80* (2013.01)

(58) Field of Classification Search
CPC ........ G01N 33/50; G01N 33/52; G01N 33/53; G01N 33/80; Y10S 435/973; Y10S 436/808
See application file for complete search history.

(56) References Cited

U.S. PATENT DOCUMENTS

| 4,756,884 | A * | 7/1988 | Hillman | B01F 5/0646 366/DIG. 3 |
| 9,415,390 | B2 * | 8/2016 | Gumbrecht | B01L 3/502715 |
| 9,442,108 | B2 * | 9/2016 | Clime | G01N 33/54306 |
| 2005/0130292 | A1 * | 6/2005 | Ahn | A61B 5/14532 435/287.1 |
| 2006/0105402 | A1 * | 5/2006 | Rott | G01N 33/5302 435/7.21 |
| 2011/0275162 | A1 * | 11/2011 | Xie | G01N 21/8483 436/164 |

FOREIGN PATENT DOCUMENTS

| DE | 41 24 778 | | 1/1993 |
| EP | 0 485 228 | | 5/1992 |
| EP | 0 542 655 | | 5/1993 |
| EP | 0 760 103 | | 11/1995 |
| FR | 2 673 472 | | 9/1992 |
| FR | 2 937 143 | | 4/2010 |
| WO | WO 86/03008 | | 5/1986 |
| WO | WO 95/30904 | | 11/1995 |
| WO | WO 01/73426 | | 10/2001 |
| WO | WO 2006/051548 | | 5/2006 |
| WO | WO 2007/092028 | | 8/2007 |
| WO | WO 2011/036289 | * | 3/2011 ............... B01L 3/00 |

OTHER PUBLICATIONS

International Search Report and Written Opinion from International Application No. PCT/EP2012/074481 dated Feb. 13, 2013.
Malomgré et al., "Recent and future trends in blood group typing", *Anal Bioanal Chem*, vol. 393, 2009, pp. 1443-1451.

* cited by examiner

*Primary Examiner* — Gary Counts
(74) *Attorney, Agent, or Firm* — Merchant & Gould P.C.

(57) ABSTRACT

An assaying kit is for pre-transfusion blood group matching between two blood samples. The kit includes at least two assemblies (101,201) corresponding to the first and the second blood sample, each assembly has at least two test units (1). Each test unit (1) includes a reagent containing an antigen present on erythrocytes or an antibody able to bind to an antigen present on erythrocytes. Each test unit (1) also includes a membrane (2) permeable to free erythrocytes (6) and impermeable to hemagglutinated erythrocytes. The antibody contained in the first test unit for both the first assembly (101) and the second assembly (201) corresponds to a first blood group and the antibody contained in the second test units for both the first assembly (101) and the second assembly (201) corresponds to a second blood group.

13 Claims, 3 Drawing Sheets

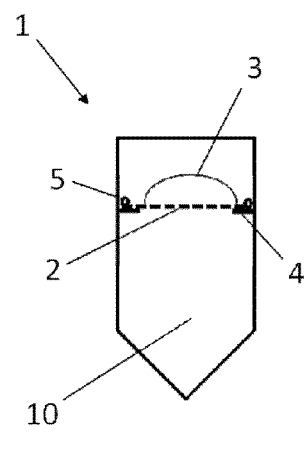
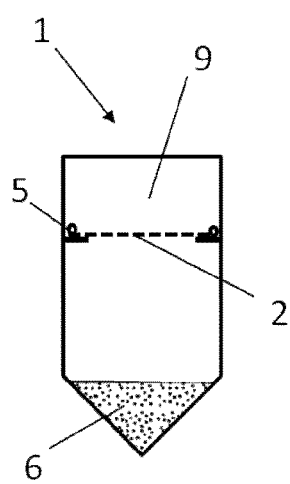
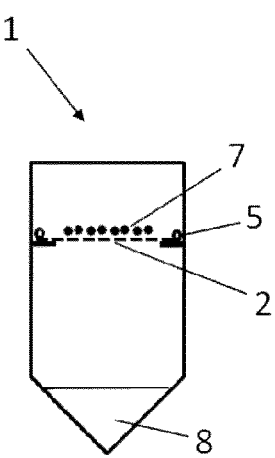
Fig. 1  Fig. 2  Fig. 3
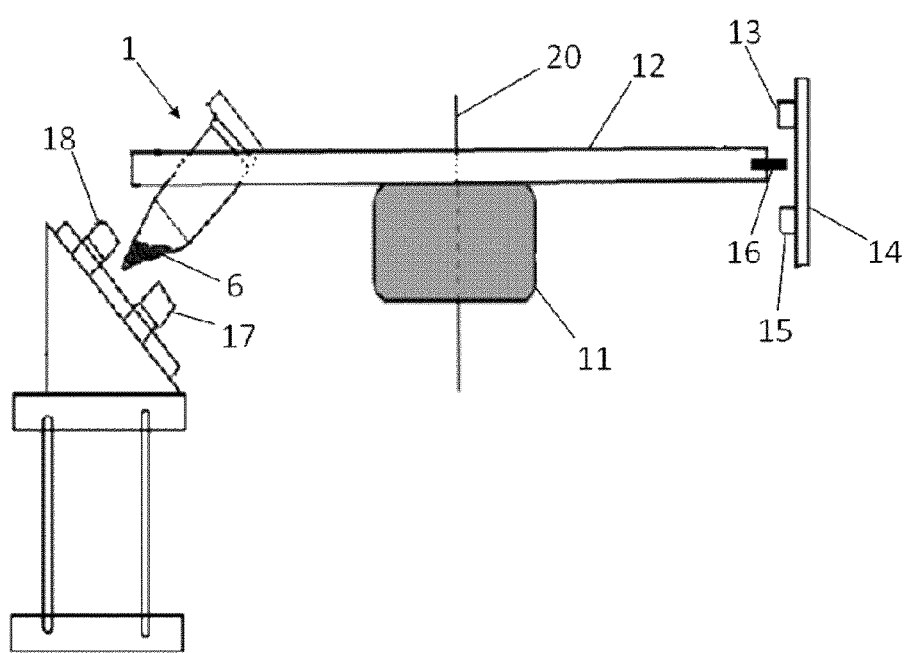
Fig. 4

METHOD AND DEVICE FOR ASSAYING AN ANTIGEN PRESENT ON ERYTHROCYTES OR AN ANTIBODY BINDING TO AN ANTIGEN PRESENT ON ERYTHROCYTES

This application is a National Stage Application of PCT/EP2012/074481, filed 5 Dec. 2012, which claims benefit of Ser. No. 11/192,236.5, filed 6 Dec. 2011 in Europe and which applications are incorporated herein by reference. To the extent appropriate, a claim of priority is made to each of the above disclosed applications.

The present invention relates to methods and devices used to ascertain a type of blood group to perform a blood compatibility pre-transfusion test.

It has been known from EP 0542655 and FR 2 673 472 to test, based on agglutination utilizing glass beads for separating hemagglutinated erythrocytes from free erythrocytes. A disadvantage is that the test is not mechanically stable. Another inconvenience is that a detection machine cannot read the result immediately. Neither can the cut-off point (size of the particles able to pass through the glass beads) be clearly defined. This method can be used directly for performing tests involving agglutinating antibodies.

However, if non-agglutinating antibodies (for instance IgG antibodies in the Coombs test) are involved, erythrocytes will first have to be washed after the incubation period in order to remove the non-bound antibodies. Only then can these erythrocytes (sensitized or not) be introduced into the test system in the presence of antiglobulin serum, whereafter agglutination can take place. So the disadvantage of this test system is that in the antiglobulin test the incubation phase and the washing phase cannot take place in the same reaction vessel.

It is also known from EP 0760103 to use a grafted membrane on which one or more immunoglobulin-binding substances are immobilized. Sensitized erythrocytes can be bound to this permeable solid phase. Erythrocytes on which no antibodies (immunoglobulins) are present will not be bound to the solid phase and can simply pass it because the solid phase is permeable to erythrocytes. The test is not based on hemagglutination.

Other in vitro methods (see e.g. WO 2008/148890) comprise bringing a sample into contact with distinguishable (i.e. having markers) beads on which erythrocytes or erythrocyte membrane fragments or their antibodies are attached. However, before carrying out the analysis step, as much unbound reagent as possible should be eliminated in order to reduce the background noise and therefore to obtain good specificity of the test. Washing conditions that are too drastic could reduce the sensitivity of the test.

Human errors alas remain in blood transfusions by using donor's red blood cells (RBCs), incompatible with the blood from the recipient (i.e. the individual transfused), triggering adverse reactions stemming from haemolysis or hemagglutination. There is a need of providing at the very place of blood transfusion, quick verification tests.

In transfusion medicine there is also a need for methods and device which are simple. In order to enhance transfusional security there is also a need for a clear correct interpretation of the results. There is a need of providing compatibility tests which excel at achieving an original result again by repeating the test. There is a need of providing compatibility tests which remain stable under mechanical stress. There is a need of providing compatibility tests which are easy to produce.

The present invention therefore aims to provide methods and devices that allow to obviate drawbacks of the prior art.

In particular, an aspect of the invention aims to provide methods and devices enabling to ascertain a type of blood group and/or to perform a pre-blood transfusion bedside test so that errors in blood transfusion can be avoided.

Some aspects of the invention also aims to provide methods and devices which enable to shorten the time needed for compatibility matching, e.g. by making steps like washing omissible, for example when IgG (immunoglobulin of class G) is involved.

Some aspects of the invention also aims to provide methods and devices which enable blood group testing and/or compatibility tests at the very place of blood transfusion (POCT: point of care tests) by providing easily carriable or easily moveable or portable equipment necessary for matching.

It is also an aim of the invention to provide methods and devices which are simple.

Some aspect of the invention also aims to provide methods and devices of which the interpretation of the results by naked eye and/or automatically by a machine, are clear and correct. The latter can be obtained by a clearly defined cutoff point.

Some aspect of the invention also aims to provide reproducible compatibility tests.

Some aspect of the invention also aims to provide compatibility tests which remain stable under mechanical stress like centrifugation, pressure and/or vibration. Mechanical stress can be caused by moving the test.

Some aspect of the invention also aims to provide compatibility tests which are easy to produce. The latter reduces production costs.

SUMMARY OF THE INVENTION

The present invention is related to a method for assaying (detecting the presence) an analyte present (artificially or naturally) in a biological sample, said analyte being a first member of a binding pair, said binding pair consisting of an antigen present on erythrocytes and an antibody binding to said antigen present on erythrocytes, said method comprising the step of:

- treating the biological sample with a reagent containing the second member of the binding pair to generate hemagglutination in a test unit,
- separating by filtration through a membrane permeable to free erythrocytes and impermeable to hemagglutination, the hemagglutination, if any has formed, from the free erythrocytes, and
- detecting said free erythrocytes and/or said hemagglutination and correlating the presence of the analyte in the sample through the detection of free erythrocytes downstream of the membrane and/or hemagglutination upstream of the membrane.

Advantageously, the upper and lower limits of the pores sizes of the membrane can be combined to yield optimal porosity ranges, depending on the erythrocyte size in the biological sample (i.e. mainly depending on the species from which the erythrocyte originates). The lowest porosity limit for the membrane is the diameter of the involved free cell from a species; the diameter of a human RBC is 6 to 8 μm. Included in the porosity range is two times the diameter of the involved free cell. Preferably, the membrane has a porosity comprised between 6 μm and 25 μm.

Advantageously, the membrane is free of an analyte-binding material.

Preferably, the membrane or a layer thereof is selected from the group consisting of woven tissue, non woven tissue, track-etched membrane and a porous film or a combination thereof. More preferably, the membrane or a layer thereof comprises (or essentially consist of) polyamide.

Advantageously, the filtration is promoted by centrifugation, capillarity, vacuum downstream of the membrane, overpressure upstream of the membrane or a combination thereof. Preferably, in case of vacuum or overpressure, the difference of pressure should be adapted to avoid hemolysis.

Advantageously, the analyte to be assayed is a blood group antigen present on erythrocytes or an antibody binding to a blood group antigen.

Preferably, the free erythrocytes or the hemagglutination is detected by optical means, such as preferably IR absorption measurements. Alternatively or in combination of optical detection, the detection can be done or checked by visual observation.

Advantageously, the detection of the erythrocytes or the hemagglutination is compared with an assay without the second member of the binding pair (blanco).

Preferably, the biological sample comprises whole blood.

Advantageously, at least two analyte are assayed simultaneously in two separate test units, a first analyte corresponding to A blood group antigen or antibody binding to the said antigen and the second analyte is corresponding to B blood group antigen or antibody binding to the said antigen.

Preferably, a third test unit is used for assaying an analyte corresponding to Rh blood group antigen or antibody binding to the said antigen.

A second aspect of the invention is related to a method for verifying (transfusional) compatibility matching wherein the blood group antigens or antibodies of two biological samples are tested essentially simultaneously by the method of the invention, the two biological samples corresponding to a first individual and a second individual and wherein the results are compared for compatibility matching.

Advantageously, the first individual is corresponding to a donor, and the second individual is corresponding to a recipient. More preferably the compatibility matching verification is performed at the point of care (recipient's room) just before administration of a transfusion.

Preferably, the results are further compared to predetermined data stored in a database.

A third aspect of the invention is related to a kit suitable for use in the process according to the second aspect of the invention for (transfusional) compatibility matching between two samples, said kit comprising at least two test units for the first sample and two test units for the second sample, each unit comprising:

- a reagent containing an antigen present on erythrocytes or an antibody able to bind to an antigen present on erythrocytes, and
- a membrane permeable to free erythrocytes and impermeable to hemagglutination, wherein the antigen or antibody contained in the first test units for both the first sample and second sample is corresponding to a first blood group (A) and the antigen or antibody contained in the second test units for both the first sample and second sample is corresponding to a second blood group (B).

Preferably, the kit of the invention further comprises filtering promotion (centrifugation) means for generating a flow of the biological sample through the membrane.

Advantageously, the test units comprises a first cavity for receiving the reagent and the biological sample and a second cavity for receiving the filtrate, the first and second cavity being separated by the membrane.

Advantageously, the kit further comprise optical means for detecting free erythrocytes in the second cavity and/or for detecting hemagglutination on the membrane. More preferably, optical detection is performed on both the membrane and the second cavity for improving reliability of the test.

Advantageously, the test units corresponding to each sample are assembled in assemblies, one assembly corresponding to a donor blood sample, and one assembly for the recipient blood sample.

Preferably, each assembly is produced in one part, for example by polymer injection molding.

Another aspect of the invention, is related to a procedure for reducing the probability of ABO compatibility mistakes wherein the method for assaying an analyte in a biological sample, said analyte consisting of an antigen present on erythrocytes or an antibody binding to an antigen present on erythrocytes is used as POCT. Preferably in said procedure telecommunication means are used to compare the results of the method for assaying with a database of a central laboratory, permitting an additional verification of the compatibility match.

BRIEF DESCRIPTION OF THE DRAWINGS

FIG. 1 represents an example of a test unit used according to one preferred embodiment of the invention before testing.

FIG. 2 represents an example of a test unit used according to one preferred embodiment of the invention after testing, with free erythrocyte passing through the membrane.

FIG. 3 represents an example of a test unit used according to one preferred embodiment of the invention after testing, with agglutinated erythrocyte on the membrane.

FIG. 4 represents an example device used in an embodiment of the invention.

FIGURE KEYS

Figure 5:
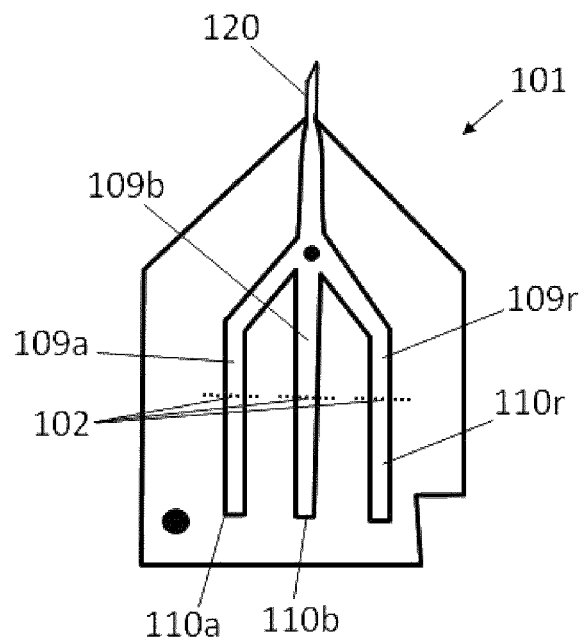
FIG. 5 represents an example of an assembly for testing a donor sample (first assembly).
Figure 6:
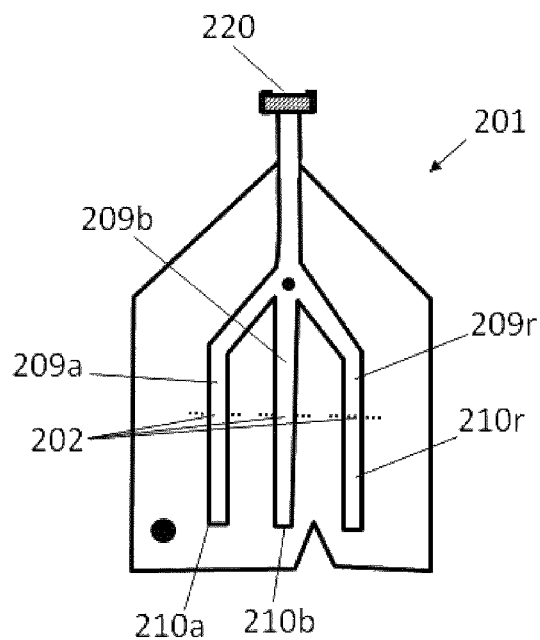
FIG. 6 represents an example of an assembly for receiving a recipient sample (second assembly)
Figure 7:
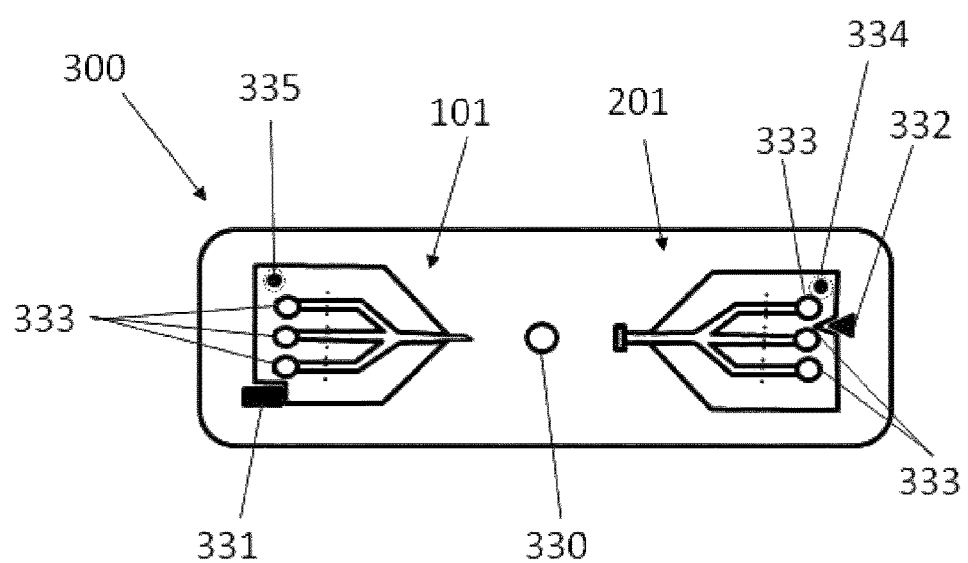
FIG. 7 represents an example of a rotating support with a first and a second assembly.

1. Test unit
2, 102, 202. Membrane
3. Biological sample mixed with reagents
4. Membrane support
5. Seal ring
6. Liquid comprising free erythrocytes
7. Agglutinated erythrocytes
8. Filtrate essentially free of erythrocyte
9, 109, 209. First cavity (upper chamber), a, b and r indices corresponding to A and B bloodgroup, and r corresponding to a reference (or control unit)
10, 110, 210. Second cavity (lower chamber), a, b and r indices corresponding to A and B bloodgroup, and r corresponding to a reference (or control unit)
11. Motor
12. Rotor
13. Optical sensor for sensing rotor position
14. Position sensor for sensing rotor position
15. LED
16. Position marker
17. IR LED
18. IR sensor
19, 330. Rotor axis 101 first assembly
201 second assembly
300 rotating support

DETAILED DESCRIPTION OF THE INVENTION

In the present invention, "pre-transfusion blood group matching between two blood samples" or "pre-transfusion blood compatibility testing" are to be considered as equivalent, as the blood group testing is performed in order to verify the blood group compatibility between a donor and a recipient.

Aspects of the invention relate to assaying an antigen (Ag) present on RBCs or an antibody (Ab) binding to an antigen (Ag) present on RBCs.

Aspects of the invention preferably relate to assaying a blood group Ag or an Ab binding to a blood group Ag. Aspects of the invention preferably relate to assaying blood group antigens or antibodies binding to blood group antigens.

There naturally or artificially are in fact, at the surface of erythrocytes, id est RBCs, membrane antigens, in particular blood group (or system) antigens or viral antigens, capable of being recognized by the immune system. A blood group antigen present on erythrocytes is intended to mean any antigen of the non-exhaustive list of the ABO system with the A antigen, the B antigen, the A and B antigens expressed simultaneously or the H antigen, of the Rhesus system with the D, E, e, and C or c antigens, of the Kell system with the K or k antigen, of the Duffy system (Fya, Fyb), of the Kidd system (Jka, Jkb) system or else of other systems, such as MNSs, Lewis, Lu, P1, Lea, Leb, Cw, M, N, S, s etc.

The most clinically significant Ag system is the ABO RBC Ag system, which is unique inasmuch as the majority of human individuals produce Abs to those Ags without having been actively immunized against them. Thus, an individual's RBCs may display either A, B or both A and B Ags. About 40% of the population does not carry either of these Ags and is therefore, typed or grouped as O or Zero. The plasma or serum in blood of group O individuals has Abs against both A and B group Ags. The plasma or serum in blood of group AB individuals, however, does not demonstrate Abs to either A or B group Ags. Accordingly, the plasma or serum in blood of group A individuals has Abs against B group Ags, while the plasma or serum in blood of group B individuals has Abs against A group Ags.

Incompatibility in the ABO Ag system will result in strong adverse reactions, which can be prevented by matching the first individual e.g. the donor to the second individual e.g. the recipient. Ideally, the donor and recipient should belong to the same blood group; however, in the absence of an identical donor, an alternative blood group may be suitable as long as the recipient serum or plasma does not carry natural Abs against the donor RBCs. Thus O group is the universal donor, since its RBCs will not react with either anti-A or anti-B Abs, which are present in the blood of all other groups. Individuals of group AB can receive blood from all blood groups, since they do not have Abs to any of them.

The RBCs of an individual can either carry the rhesus (Rh) (or D) antigen (Ag) (Rh<+> or Rh-positive) or not carry it (Rh–> or Rh-negative). Unlike the ABO Ag system, anti-Rh (anti-D) Abs are not normally present in the blood Rh-negative individuals. Such Abs nevertheless develop in Rh-negative individuals following an immunological potentiation resulting from a transfusion with Rh-positive blood or from pregnancy with an Rh-positive fetus. Matching of Rh between donor and recipient, in addition to ABO matching, can be done to prevent generation of Rh Abs in Rh-negative individuals and to prevent adverse reactions in individuals that may carry anti-Rh Abs.

Besides the A, B and Rh Ags, RBCs may carry a variety of other Ags, which are sometimes referred to as sub-groups. Similarly to the Rh Ag (and to most Ags in nature), Abs to those Ags are not normally present in human blood, but may arise due to previous blood transfusions or pregnancy with an Ag-carrying fetus. Such Abs are referred to as unexpected.

Some antibodies against RBC antigens are considered 'incomplete' inasmuch as they are not able to agglutinate RBCs directly but require the addition of an anti-globulin (Coombs' reagent) to facilitate agglutination.

The reagent might contain Liss medium and/or Coombs reagent.

In the present invention, the biological sample to be tested may originate from humans, including at a developmental stage before birth. Alternatively, the biological sample to be tested may originate from any animal having a plurality of antigenic molecules. Animals may, for example, be the dog, in which eight different blood groups have been identified to date, the cat, which has three, . . . .

Biological sample is intended to mean any body fluid or tissue biopsy that comprises erythrocytes or anti-erythrocyte antibodies, whether physiologically or pathologically. The latter can be supernatant of a hybridoma. As a biological sample, mention may therefore be made of a blood sample, and in particular a whole blood sample or a blood cell pellet sample (or a blood bag), or any other blood preparation, but also saliva, sweat, tears, breast milk, faeces or urine when it contains blood or antibodies. It is also possible to use a plasma or blood serum sample. Said biological sample can also be a mixture comprising: body fluid, tissue biopsy, blood sample, other blood preparation, plasma, blood serum, saliva, sweat, tears, breast milk, faeces or urine.

An antibody (Ab) binding to an antigen (Ag) present on erythrocytes denotes any antibody against antigenic molecules carried by erythrocytes or any anti-erythrocyte antibody.

According to the invention, Ab refers to IgA, IgD, IgE, IgG and/or IgM (immunoglobulin of class M).

Antibody refers to any whole antibody or functional fragment (hypervariable portion) of an antibody comprising or consisting of at least one antigen combination site, which allows said antibody to bind to at least one antigenic determinant of an antigenic compound. By way of example of antibody fragments, mention may be made of Fab, Fab' and F(ab')2 fragments and also scFv chains (single chain variable fragment), dsFv chains (double-stranded variable fragment), etc.

Antibodies contained by a reagent may be polyclonal or monoclonal antibodies. The production of monoclonal antibodies or of polyclonal antibodies that can be used in the context of the invention comes under conventional techniques; Abs can be purchased at e.g. Immucor Gamma® or Diamed®.

As shown in FIGS. 1 to 3, a membrane 2 separates free erythrocytes 6, to which it is permeable, from hemagglutinated erythrocytes 7 to which it is impermeable.

The membrane 2 advantageously does not chemically react with constituents of the analyte or/and with constituents of the reagent.

The membrane 2 of the current invention or a layer thereof is advantageously selected from the group consisting of woven tissue, non woven tissue, and porous polymeric film such as track-etched membrane or a combination thereof. Woven tissue reduces production costs by being cheap. Woven tissue has well defined pores. Porous polymeric films and track-etched membranes have the further advantage of being less sensitive to deformation, for example induced by the assembly process.

The membrane 2 of the current invention preferably consist of one single layer. Eventually, the membrane may be mechanically supported, for example by a grid.

Advantageously, the membrane 2 of the present invention is a polymeric membrane, the polymer being preferably selected from the group consisting of nylon, cellulose-ester polymer, nitrocellulose, polyvinylidene fluoride (PVDF), polytetrafluoroethylene (PTFE), polyether sulfone, polycarbonate, polyester and a combination thereof.

The porosity of the membrane 2 of the current invention is preferably monodispersed. By having a well defined size porosity, monodispersed membranes advantageously present a well defined pass-through cutoff, thereby increasing the reliability of the method of the invention. Track-etched membranes present such monodispersed porosity, with the further advantage of having narrow size dispersion.

The membrane of the current invention has a porosity chosen to be permeable to free erythrocytes and impermeable to hemagglutinated erythrocytes. Therefore, the pores of the membrane 2 are advantageously larger than or equal to about 6, about 9 or about 11 µm, and smaller than or equal to about 25, about 20, about 16, about 14 or about 13 µm. Indicated upper and lower limits can be combined to yield optimal porosity ranges, depending on the erythrocyte size in the biological sample (i.e. mainly depending on the species from which the erythrocyte originates). The lowest porosity limit for the membrane is the diameter of the involved free cell from a species; the diameter of a human RBC is 6 to 8 µm. Included in the porosity range is two times the diameter of the involved free cell. If a single IgM is involved, a pentamerous hemagglutination has a diameter of about 16 µm. In practice, multiple IgM are involved and thus the diameter will be bigger than 16 µm.

Preferably, the membrane is fixed to the inside of the test unit 1 by means of a seal ring 5 (i.e. washer). Preferably, the seal ring is rubber.

Alternatively, the membrane 2 can be glued or welded to the inside of a test unit. Welding can be done by thermal, ultrasonic, laser or radiofrequency sealing process. The assembly can also be performed by using a suitable glue and/or solvent bonding.

Preferably, mechanical stress is minimized during fixation of the membrane. Hence the porosity of the membrane remains intact. This is particularly the case for woven or non woven membranes sensitive to mechanical stress.

Advantageously, the membrane 2 is horizontally fixed to the inside of a test unit.

Preferably, the membrane 2 is situated:
  at the top of a test unit 1,
  between the top of a test unit 1 and at one third from the top of a test unit 1,
  0.5 cm from the top of a test unit 1,
  between halfway a test unit 1 and at one third from the top of a test unit 1,
  halfway a test unit 1 or
  between halfway a test unit 1 and at one third from the bottom of a test unit 1.

Preferably, the filtration across the membrane 2 is promoted by centrifugation, capillarity, vacuum in the bottom of the test unit, overpressure on top of the test unit or a combination thereof. In case of vacuum or overpressure, the difference of pressure should be adapted to avoid hemolysis. The pressure difference can for example be induced by a piston, said piston being situated at the top (overpressure) or the bottom (vacuum) of the test unit.

A test unit 1 can be a test tube, a sample tube, an Eppendorf tube or the like. Advantageously, test units 1 are made of material biocompatible with blood. Test units made of polypropylene, polymethylpentene or polycarbonate can be used. Polypropylene tubes (0.5 ml, 1.5 ml or 2 ml) of high chemical resistance, possibly free of slip agents, biocides or plasticizers, which might have a centrifugation stability up to 25,000×g in fixed-angle rotor, up to 70,000×g in swing-bucket rotor.

The test units are preferably sized to contain a maximal volume between about 0.01 ml and about 2.5 ml, preferably between about 0.02 ml and about 1 ml, preferably between about 0.04 ml and about 0.4 ml A test unit 1 can have a lid and/or a colour conform to a specific source of blood. A mould and/or a bar code system can only allow certain test units carrying a specific source of blood in certain positions. Measures described in this paragraph are there to avoid human error.

Preferably, the test unit contains an incubation chamber where binding between antibody and antigen can take place. Alternatively the binding between Ab and Ag can take place in a test unit other than the test unit with the membrane being fixed to its inside.

As represented in FIG. 1, the test unit 1 preferably comprises a first cavity 9, forming the incubation chamber, for receiving the reagent and the biological sample 3 and a second cavity 10 for receiving the filtrate (6 or 8), the first and second cavity being separated by the membrane 2.

Advantageously, the time in the incubation chamber is comprised between 40 seconds and 300 seconds, preferably between 40 seconds and 120 seconds.

Advantageously, the incubation chamber are prefilled with all reagents (except the biological sample to be tested).

It is preferred that the test unit is configured to allow that that the free erythrocytes, at the bottom of the test unit 1, can be clearly visible, by human eye or by a detection machine. Preferably the test unit 1 is transparent.

Advantageously, 'the bottom of the test unit' include a height slightly above the actual inner bottom of the test unit; which avoids yielding false positive results when for example several free RBCs which should have agglutinated and which have not bound yet, pass the membrane 2.

In case of an 1.5 ml Eppendorf tube, the detection level has a height of minimum 3 mm up from the inner bottom of the test unit. The ratio of the inner height of the tube to the detection level is about 12.

It is preferred that the test unit 1 is configured to allow that the hemagglutination 7, on top of the membrane 2, can be clearly visible, by human eye or by a detection machine.

It is even more preferred that the test unit 1 is so that the free erythrocytes 6, at the bottom of the test unit and the hemagglutination 3, on top the membrane 2, can be simultaneously visible, by human eye or by a detection machine.

Notice that "bottom" or "below" should be understood here as if the filtration occurred by gravity, i.e. "bottom" or "below" is downstream the membrane, and "above" or "upon" is upstream of the membrane relative to the filtration flow.

Preferably, the detection of the free erythrocytes 6 and hemagglutination 7 is performed by optical means, preferably comprising a light emitting diode 15 and a light sensor 13. The light wavelength used in said optical detection can be infrared (IR), near-infrared (NIR), ultraviolet (UV) or visible light.

Advantageously the method is used to assay simultaneously at least 2 analytes, in separate test units, such as A and B blood group. Additional test units may advantageously used to assay additional blood group or sub-group, such as Rhesus.

As a further advantage, the method of the present invention may be simultaneously be performed on a biological sample of a first individual and a second individual. This is particularly interesting for testing donor/recipient compatibility in transfusion procedure. Advantageously, the compatibility test is performed at the point of care, just before transfusion administration, verifying the compatibility between the blood of a blood bag (donor) and the blood of the patient to be transfused (recipient). Simultaneous testing of donor blood a patient blood moments before the actual transfusion reduces the risk for human error.

The following preferred embodiment discloses a kit of parts that further simplifies the use of the invention at the point of care, and some preferred embodiments further reduce the risks of mistakes.

According to a particular preferred embodiment, the kit for pre-transfusion testing blood group matching between two blood samples comprises two assemblies 101,201, one assembly corresponding to a donor and the other corresponding a recipient, each assembly comprising at least two test units for testing at least two blood group, and said at least two test units communicating to a channel receiving the sample from either a donor or a recipient, the blood samples being divided, in use, between the at least two test units in each assembly.

Preferably the at least two test units in each assembly correspond to A and B blood group, and the upper cavities of the test units are prefilled with the corresponding blood group antibody.

Advantageously, the two assemblies of the kit further comprises a third test unit without antibody, used as a control unit.

Preferably, the assembly corresponding to either the donor (blood bag) or recipient comprises means to avoid any confusion between them.

Usually, samples from blood bag consist in plastic tube sections, sealed on both ends. Therefore a convenient mean for avoiding confusion between donor and recipient is to add, at the end of the communication channel for receiving the sample, a hollow spike able to pierce said plastic tube on the assembly corresponding to the donor. The spike should be sufficiently long to obtain a communication between the inside of the plastic tube to take the sample, but too short to take a sample from standard blood sample tube closed by a septum. Preferably, the spike is directly molded as part of the assembly, and is a plastic spike, unable to pierce the skin of the recipient, again to avoid confusion between the recipient's sample and the donor's sample.

Usually, a blood sample is taken from the recipient in a standard blood sample tube which is closed after sampling by a septum. A convenient mean to take out the recipient sample is the use of a septum, the person operating the system using a syringe for taking the sample out of the standard blood sample tube through the sample tube septum and then introduce the syringe needle in the recipient assembly septum.

Advantageously the donor and recipients assemblies have slightly different shapes so that they cannot be permuted in the compatibility test machine. Protrusion 331,332 on a support 300 in the test machine can be used to obtain such feature, said protrusion corresponding to different undercut in the assemblies.

The donor and recipient parts also preferably comprises optical markers 335,334, for checking their presence in the compatibility test machine, and for verifying their position for the optical reading of the results.

The present invention also discloses a device for automatically assaying blood group compatibility between a donor and the recipient, said device comprising a rotating support (300), for supporting the first assembly (101) and the second assembly(201), said rotating support (300) being suitable for generating in use a flow of the blood sample through the membrane (2) by centrifugation.

Preferably, the device further comprises optical sensor(s) for detecting the presence either of hemaglutinated erythrocytes (7) on the membranes, or the presence of erythrocytes (6) downstream (10) of the membranes.

Advantageously, each assembly comprises an optical marker (335,334) for checking the presence of both assemblies, and for aligning the optical sensors with the assemblies.

Preferably, the device further comprises communication means for comparing the results of the compatibility test with predetermined compatibility data stored in a database. The examples mentioned below are all carried out at room temperature.

EXAMPLE

The device used in this experiment is represented schematically in FIG. 4. It comprises:
- a rotor 12 rotating around a vertical axes 20 and being controlled by an electrical motor 11, said rotor comprising six positions each being able to receive one test unit 1 made of a polypropylene tube of 1 cm diameter and 3.8 cm length;
- Each tube is composed of one upper chamber 9 of about 200 µl separated from a lower chamber 10 by a membrane 2 of 11 µm porosity;
- The membrane 2 consists in a piece of Millipore's 47 mm diameter with grid number 215, 6% nylon 94% emptiness, with a porosity of 11 µm. The membrane 2 is maintained in position by means of a rubber seal ring 5;
- Each tube is positioned in the rotor 12 such as the bottom of each of them interrupt the path between a LED 17 and a light sensor 18 (both in the IR region) at each rotation;
- The centrifugation device has a maximum of 1200 rotations per minute;
- The optical density was measured at the bottom of each test unit by the means of the LED 17 and light sensor 18. The results were given as a score (arbitrary unit, based on comparative data). The baseline was 200-300.

Description of Procedure

In first and fourth test units, 50 µl of monoclonal Ab anti-A (Novaclone™ murine monoclonal, manufactured by Dominion biologicals limited for Immucor Gamma) and 50 µl whole blood from first and second individual respectively were mixed.

In second and fifth test units, 50 µl monoclonal Ab anti-B (Novaclone™ murine monoclonal, manufactured by Dominion biologicals limited for Immucor Gamma) and 50 µl whole blood from first individual and second individual respectively were mixed.

Third and sixth test units are negative controls containing 50 µl whole blood from first individual and second individual respectively and 50 µl physiologic serum (Sterile NaCl solution 0.9% from B Braun).

The six units were placed in the rotor and centrifuged at 900 rotations per minute. The rotor diameter was about 20 cm Results Example 1

Normal blood samples were collected in Citrate, EDTA or SAGM.

In three different polypropylene tubes, 50 µl of whole blood were mixed with 50 µl of either anti-A monoclonal Ab (Anti-A Novaclone™ murine monoclonal, manufactured by Dominion biologicals limited for Immucor Gamma), anti-B monoclonal Ab (Anti-B Novaclone™ murine monoclonal, manufactured by Dominion biologicals limited for Immucor Gamma)) or Sterile NaCl solution 0.9% (from B Braun). The incubation time was 60 seconds. Each mixture was transferred on top of the membrane (a piece of Millipore's 47 mm diameter with grid number 215, 6% nylon 94% emptiness, with a porosity of 11 µm) fixed to the inside of a tube (1.5 ml Eppendorf) before centrifugation during 3 min at 900 rotations per minute. By means of a rubber seal ring, the membrane is horizontally situated 0.5 cm from the top of the Eppendorf unit.

The optical density was measured by the IR LED and IR sensor in the bottom of each unit.

The results were given a score. When hemagglutination did not form on the membrane, scores higher than 600 (with a maximum of 800) were observed. When hemagglutination did form on the membrane, scores lower than 600 were observed. The baseline was 200-300.

The results were compared to those from the routine method of the laboratory e.g. gel technique (available from DiaMed), in which a mixture of 12.5 µl of a 0.8% RBCs suspension and 50 µl antibody was forced into the gel by centrifugation (with an acceleration of about 90 g). Agglutinated RBCs were not be able to penetrate the gel and stayed on top of the gel. Non-agglutinated cells permeated the gel column and got to its bottom. Small size agglutinates entered the gel column but did not get to its bottom.

The results from both techniques for blood groups were:
26 A, 9 B and 22 0 for Citrate,
18 A, 9 B, 2 0 and 1 AB for EDTA and
14 A, 26 B and 14 0 for SAGM.

Example 2

Pathologic samples were collected in EDTA. In three different polypropylene tubes, 50 µl of whole blood were mixed with 50 µl of either anti-A monoclonal Ab (Anti-ANovaclone™ murine monoclonal, manufactured by Dominion biologicals limited for Immucor Gamma), anti-B monoclonal Ab (Anti-B Novaclone™ murine monoclonal, manufactured by Dominion biologicals limited for Immucor Gamma) or Sterile NaCl solution 0.9% (from B Braun). The incubation time was 60 seconds. Each mixture was transferred on top of the membrane (a piece of Millipore's 47 mm diameter with grid number 215, 6% nylon 94% emptiness, with a porosity of 11 µm) fixed to the inside of a tube before centrifugation during 3 min at 900 rotations per minutes.

The optical density was measured by the IR LED and IR sensor in the bottom of each unit.

The results were given a score. When hemagglutination did not form on the membrane, scores higher than 600 (with a maximum of 800) were observed. When hemagglutination did form on the membrane, scores lower than 600 were observed. The baseline was 200-300.

The results from both techniques for blood groups were:
2 A, 1 B and 4 0 for 7 patients with sickle cell anaemia,
0 A, 2 B, 8 0 and 0 AB for 10 anaemia patients (Hb: 5.8-7.7 g/dL; HCT: 17.5-23.9),
1 A, 1 B and 2 0 for 4 newborns (attenuated antigen expression) and
24 consistent results for 24 samples from microcytose patients (MCV: 57-79 fl)

It can be clearly deduced from the above mentioned comparative data that the ABO group was verified.

Example 3

In 18 different test units, 50 µl of whole blood of macrocytose patients (MCV: 101-135 fl) was mixed with 50 µl Sterile NaCl solution 0.9% (from B Braun). Each mixture was directly transferred on top of the membrane (a piece of Millipore's 47 mm diameter with grid number 215, 6% nylon 94% emptiness, with a porosity of 11 µm) fixed to the inside of a tube (1.5 ml Eppendorf) before centrifugation during 3 min at 900 rotations per minute. By means of a rubber seal ring, the membrane is horizontally situated 0.5 cm from the top of the Eppendorf unit.

There was complete passage of the RBCs whatever the MCV value. This confirms suitability the selected porosity of the membrane even for pathological samples.

The invention claimed is:

1. An assaying kit for testing pre-transfusion blood group matching between two blood samples, said kit comprising:
    a donor assembly corresponding to a first donor blood sample, the donor assembly having a first shape; and
    a recipient assembly corresponding to a second recipient blood sample, the recipient assembly having a second shape different from the first shape to avoid confusion with the donor assembly;
    each assembly comprising at least two test units, each test unit comprising:
        a reagent containing an antibody able to bind to an antigen present on erythrocytes, and
        a membrane permeable to free erythrocytes and impermeable to hem agglutinated erythrocytes,
        a first cavity for receiving the reagent and the donor blood sample or the recipient blood sample, and a second cavity for receiving a filtrate; the first cavity and the second cavity being separated by the membrane;
    wherein the antibody contained in the first test unit for both the first donor assembly and the second recipient assembly corresponds to a first blood group, the antibody contained in the second test units for both the first donor assembly, and the second recipient assembly corresponds to a second blood group;
    wherein each assembly comprises means for receiving a blood sample and distributing said blood sample between the test units of each assembly; and
    wherein the means for receiving the blood sample of the assembly corresponding to the first donor blood sample comprise a needle for taking a blood sample from a blood bag, said needle comprising a tip incapable of piercing skin of an individual to inhibit receiving a sample directly sampled from an individual.

2. The assaying kit according to claim 1 wherein the antibody contained in the first test unit of each assembly is corresponding to blood group A and the antibody contained in the second test unit of each assembly is corresponding to blood group B.

3. The assaying kit according to claim 1 wherein each of the assemblies of the kit further comprises a third test unit without antibody, used as a control unit.

4. The assaying kit according to claim 1 wherein each of the assemblies of the kit further comprises an additional test unit containing an antibody corresponding to the Rhesus (Rh) blood group.

5. The assaying kit according claim L wherein the means for receiving the blood sample of the assembly corresponding to the first donor blood sample further comprises a hollow needle configured to pierce a plastic tube of a blood bag to take a blood sample and said hollow needle having insufficient sharpness to directly take a blood sample from an individual.

6. The assaying kit according to claim 1, wherein the means for receiving the blood sample of the assembly corresponding to the second recipient blood sample further comprises means for receiving a blood sample from a syringe, said means being adapted to prevent taking a sample directly from a blood bag or a blood bag tubing.

7. The assaying kit according to claim 6 wherein the means for receiving the blood sample of the assembly corresponding to the second recipient blood sample further comprises a female luer or a septum able to receive a blood sample from a syringe.

8. The assaying kit according to claim 1, further comprising a device comprising a rotating support, for supporting the first donor assembly and the second recipient assembly, said rotating support being configured for generating in use a flow of the blood sample through the membrane by centrifugation.

9. The assaying kit according to claim 8 wherein the device further comprises an optical sensor for detecting the presence either of hemaglutinated erythrocytes on the membranes, or of erythrocytes downstream of the membranes.

10. The assaying kit according to claim 9 wherein each assembly comprises an optical marker for checking presence of both assemblies, and for aligning the optical sensor with the assemblies.

11. The assaying kit according to claim 8 wherein the device further comprises communication means for comparing results from the optical sensor with predetermined compatibility data stored in a database.

12. The assaying kit according to claim 5, the hollow needle comprising a plastic spike, the plastic spike having insufficient sharpness to pierce the skin of the recipient.

13. The assaying kit according to claim 12, wherein the spike is directly molded as an integral portion of the assembly corresponding to the first donor blood sample.

* * * * *